US010398692B2

(12) United States Patent
Borgman et al.

(10) Patent No.: US 10,398,692 B2
(45) Date of Patent: Sep. 3, 2019

(54) TERCONAZOLE COMPOSITION AND METHOD

(71) Applicant: Curatek Pharmaceuticals Holding, Inc., Elk Grove Village, IL (US)

(72) Inventors: Robert J. Borgman, Mundelein, IL (US); James E. Juul, Wauconda, IL (US)

(73) Assignee: Curatek Pharmaceuticals Holding, Inc., Elk Grove Village, IL (US)

( * ) Notice: Subject to any disclaimer, the term of this patent is extended or adjusted under 35 U.S.C. 154(b) by 621 days.

(21) Appl. No.: 14/728,190

(22) Filed: Jun. 2, 2015

(65) Prior Publication Data

US 2015/0265609 A1 Sep. 24, 2015

Related U.S. Application Data

(63) Continuation-in-part of application No. 11/519,303, filed on Sep. 12, 2006, now Pat. No. 9,211,286.

(51) Int. Cl.
*A61K 31/496* (2006.01)
*A61K 47/12* (2006.01)
*A61K 47/38* (2006.01)
*A61K 9/00* (2006.01)

(52) U.S. Cl.
CPC .......... *A61K 31/496* (2013.01); *A61K 9/0014* (2013.01); *A61K 9/0036* (2013.01); *A61K 47/12* (2013.01); *A61K 47/38* (2013.01)

(58) Field of Classification Search
CPC ... A61K 2300/00; A61K 31/496; A61K 47/12
See application file for complete search history.

(56) References Cited

U.S. PATENT DOCUMENTS

2003/0130225 A1* 7/2003 Ahmad et al. .................. 514/45

\* cited by examiner

*Primary Examiner* — Johann R Richter
*Assistant Examiner* — Danielle Sullivan
(74) *Attorney, Agent, or Firm* — Olson & Cepuritis, Ltd.

(57) ABSTRACT

An aqueous terconazole composition comprises at least about 0.4 percent by weight of terconazole dissolved in water, and a terconazole crystallization-inhibiting amount of citric acid. The composition is free from terconazole crystals at an ambient temperature of about 20° C. Methods of preparing the composition are also described. The compositions provide for improved therapeutic release of terconazole.

11 Claims, 1 Drawing Sheet

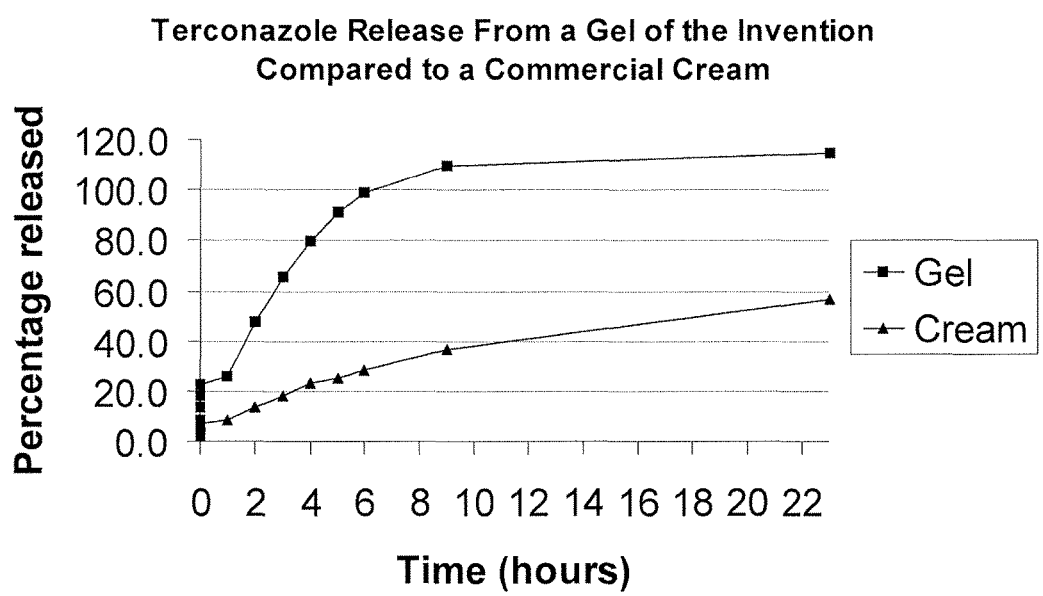

TERCONAZOLE COMPOSITION AND METHOD

CROSS-REFERENCE TO RELATED APPLICATION

This application is a continuation-in-part of U.S. patent application Ser. No. 11/519,303, filed on Sep. 12, 2006, which is incorporated herein by reference in its entirety.

FIELD OF THE INVENTION

The invention relates generally to compositions comprising terconazole, which are useful for treatment of microbiological infections. More particularly, the invention relates to aqueous solutions of terconazole and methods of preparing said solutions.

BACKGROUND OF THE INVENTION

Terconazole (cis-1-[p[[2-(2,4-dichlorophenyl)-2-(1H-1,2,4-triazol-1-ylmethyl)-1,3-dioxolan-4-yl]methoxy]phenyl]-4-isopropylpiperazine) ($C_{26}H_{31}Cl_2N_5O_3$) is a drug which has been useful for treatment of vaginal yeast infections as a cream containing about 0.4 or 0.8 percent by weight terconazole.

Terconazole is substantially insoluble in water. Terconazole has a solubility of about 0.007 percent by weight in water. Because of this low solubility, it is difficult to obtain stable terconazole solutions in water at concentrations required for therapeutic effect.

There is a need for aqueous terconazole solutions that include a relatively high amount of dissolved terconazole, and which are free from terconazole crystals. Such solutions are useful in the preparation of pharmaceutical products for the treatment of yeast infections. Viscous aqueous compositions are particularly desirable, because they provide rapid release of the terconazole and generate the relatively high terconazole concentrations required for rapid killing of pathogens. The present invention provides such aqueous terconazole compositions.

SUMMARY OF THE INVENTION

An aqueous terconazole composition of the invention comprises at least about 0.4 percent by weight of terconazole dissolved in water, and a terconazole crystallization-inhibiting amount of citric acid. The composition is free from terconazole crystals at an ambient temperature of about 20° C. The compositions are useful for treating vaginal yeast infections.

In a preferred embodiment, the composition contains about 0.8 to about 3 percent by weight of terconazole dissolved in water. Citric acid is present in the composition in a molar amount of at least 35 mole percent, preferably in the range of about 50 to about 150 mole percent, based on the molar amount of dissolved terconazole, more preferably at least equal to the molar amount of dissolved terconazole. Optionally, viscosity modifying agents, such as thickeners, can be included in the compositions of the invention to provide gels particularly suitable for vaginal or topical application.

A method aspect of the present invention involves preparing an aqueous solution of terconazole comprising at least about 0.4 percent by weight of terconazole dissolved in water and free from terconazole crystals at ambient temperature of about 20° C.

BRIEF DESCRIPTION OF THE DRAWINGS

FIG. 1 depicts a graph of improved terconazole release versus time for a gel composition of the invention containing dissolved terconazole (labeled "Gel") as compared to a commercial terconazole cream (labeled "Cream").

DETAILED DESCRIPTION OF PREFERRED EMBODIMENTS

The terms "pharmaceutically acceptable", "physiologically tolerable", "physiologically compatible", and grammatical variations thereof, as used herein and in the appended claims as they refer to electrolytes (e.g., salts), bases, diluents, preservatives, buffers and other excipients, are used interchangeably and represent that the materials are capable of topical administration to human skin and to the human vagina without the production of medically unacceptable levels of undesirable physiological effects such as irritation, itching, stinging, or systemic effects such as nausea, dizziness, and the like.

The present invention provides aqueous terconazole solutions having a concentration of dissolved terconazole of at least about 0.4 percent by weight, which are free from terconazole crystals. In the solutions of the present invention, terconazole is solubilized by the presence of a terconazole crystallization-inhibiting amount of citric acid. The compositions preferably have an acidic pH value in the range of about 3.5 to about 4.5.

Preferably, the citric acid is present in the composition at a concentration in the range of about 50 to about 150 mole percent based upon the molar amount of terconazole dissolved in the composition. More preferably, the citric acid is present in the composition in a molar amount at least about equal to the molar amount of terconazole dissolved in the composition.

The compositions of the present invention optionally can include a physiologically tolerable preservative, as well as pharmaceutically acceptable excipients, so long as the optional components do not interfere with the solubility of the terconazole.

Suitable physiologically tolerable preservatives include bacteriostats, preservatives, inhibitors, and the like, such as methyl, ethyl, propyl, and butyl esters of parahydroxybenzoic acid (parabens); propyl gallate; sorbic acid and its sodium and potassium salts; propionic acid and its calcium and sodium salts; 6-acetoxy-2,4-dimethyl-m-dioxane; 2-bromo-2-nitropropane-1,3-diol; salicylanilides such as dibromosalicylanilide and tribromosalicylamilide, the cis isomer of 1-(3-chloroallyl)-3,5,7-triaza-1-azanidadamantane chloride; hexachlorophene; sodium benzoate; chelating agents such as ethylene diaminetetraacetic acid (EDTA), and their alkali metal salts; phenolic compounds such as butyl hydroxyanisole, butylhydroxytoluene, chloro- and bromo-cresols, and the like; quaternary ammonium compounds such as benzalkonium chloride; aromatic alcohols such as 2-phenylethyl alcohol and benzyl alcohol; chlorobutanol; quinoline derivatives such as iodochlorohydroxyquinoline; and the like.

Pharmaceutically acceptable excipients that can be included in the compositions of the present invention include, for example, physiologically tolerable thickeners, surfactants, colorants, fragrances, water-soluble or water-miscible co-solvents, and the like, which are well known in the art. The compositions of the invention can be free-flowing solutions or gels.

Gelled compositions include a gelling or thickening agent, preferably a cellulosic thickening agent such as a hydroxypropyl methylcellulose (hypromellose), carboxymethyl cellulose, methyl cellulose, and the like.

The present invention also provides a method for preparing a solution comprising at least about 0.4 percent by weight of terconazole dissolved in water, free from terconazole crystals at an ambient temperature of about 20° C. The method comprises dissolving terconazole in an aqueous solution containing a terconazole crystallization-inhibiting amount of citric acid as described hereinabove.

The solution contains at least 35 mole percent of citric acid, preferably about 50 to about 150 mole percent of citric acid, based on the number of moles of terconazole dissolved. In preparing the solution, preferably citric acid is dissolved first, followed by introduction of terconazole. Citric acid and terconazole can also be added to water concurrently, in which case terconazole is dissolved in the citric acid solution as the citric acid solution is produced.

Preferably, an amount of terconazole is dissolved in the solution to obtain a terconazole concentration of about 0.4 to about 0.8 percent by weight. In other preferred embodiments, the solution comprises up to about 3 percent by weight terconazole, based on the total weight of the composition. The concentration of citric acid in the terconazole containing solution preferably is at least about equal to the molar amount of terconazole dissolved in the solution.

Another aspect of the present invention is an article of manufacture comprising packaging material and at least one terconazole composition of the invention in at least one sealed container within the packaging material. Preferably, the compositions are gels containing a thickening agent, preferably a cellulosic thickening agent such as hydroxypropyl methyl cellulose and the like, which provides a hydrophilic matrix for terconazole. The container comprises a label that includes printed indicia describing the contents, such as a listing of ingredients, the manufacturer's name and address, and the like. Preferably, the packaging material also includes a printed insert including detailed information on the composition, its method of administration for treatment of infections, side effects, contraindications, and the like indicia, which may be required by governmental agencies responsible for regulation of pharmaceutical products. The articles of manufacture may also include applicators, such as a tubular applicator that can be used in conjunction with a storage vessel or a squeezable tube to aid in applying the compositions of the invention (e.g., into the vagina). In addition, the container can be a single use packet or a pre-filled applicator.

The following non-limiting examples further illustrate the present invention.

EXAMPLE 1

Solubilization of Terconazole in Water

Weighed amounts of terconazole were added to separate containers including an acid in water, and applying heat, if necessary, to dissolve the terconazole. The amount of acid was selected to be about equimolar with the amount of terconazole added. After the terconazole was dissolved, each solution was cooled to about 4° C. in an attempt to force crystallization of some of the terconazole. If crystals were not observed upon cooling, seed crystals of terconazole were added, and the solutions were again cooled and maintained at about 4° C. to force crystallization of some of the terconazole. After allowing for crystal formation, the solutions were allowed to warm to room temperature (about 20° C.). Each solution was observed at about 20° C. over a period of about 14 days to determine if the crystals would re-dissolve. The absence of crystals after 14 days indicates that the acid salt of the terconazole is soluble at the concentration of the prepared solution. Table 1, below, includes dissolution data for a number of compositions comprising varying amounts of terconazole and various acids. The data in Table 1 clearly indicate that solutions having a terconazole concentration of up to at least about 3 percent by weight and free from terconazole crystals at 20° C. were obtained utilizing tartaric acid and malic acid.

TABLE 1

| Formulation | Presence or Absence of Crystals After 14 Days at About 20° C. |
| --- | --- |
| Terconazole (1%) + hydrochloric acid | crystals |
| Terconazole (1%) + malic acid | no crystals |
| Terconazole (1%) + tartaric acid | no crystals |
| Terconazole (2%) + hydrochloric acid | crystals |
| Terconazole (2%) + malic acid | no crystals |
| Terconazole (2%) + tartaric acid | no crystals |
| Terconazole (3%) + hydrochloric acid | crystals |
| Terconazole (3%) + malic acid | no crystals |
| Terconazole (3%) + tartaric acid | no crystals |

In a related experiment, the solubility of terconazole in water was increased to about 2.9 percent by weight using acetic acid at pH of about 5. The solubility data are presented in Table 1A below.

TABLE 1A

| Compound | Solvent | pH | pH Adjusted With | Solubility (mg/ml) |
| --- | --- | --- | --- | --- |
| Terconazole | water | 7.1 | N/A | 0.07 |
| Terconazole | water | 4.23 | HCl | 3.4[1] |
| Terconazole |  | 4.99 | acetic acid | 29.4[2] |

[1]The solution became cloudy after six hours at ambient temperature; after 24 hours at ambient temperature a precipitate was observed.
[2]No cloudiness or precipitation was observed after 24 hours at ambient temperature.

Data in Table 1A show that a mere decrease in the pH of the aqueous terconazole solution is not sufficient to avoid crystal formation.

EXAMPLE 2

Terconazole Gel Composition

A terconazole gel composition containing citric acid was prepared from the components listed in Table 2, below. The gel was cooled to about 4° C. and seed crystals of terconazole were added in an attempt to force crystallization of some of the terconazole. No crystal formation was observed during this cooling and seeding period. The formulation was then observed at about 20° C. over a period of about 14 days to determine if terconazole crystals would form. No terconazole crystals formed during this period of time. These results clearly indicate that a gel composition having a terconazole concentration of about 2.4 percent by weight and free from terconazole crystals at 20° C. was obtained utilizing citric acid.

TABLE 2

| Ingredient | Percentage |
| --- | --- |
| Terconazole | 2.4 |
| MethoCel K 100M[1] | 2 |
| Propylene glycol | 5 |
| Methyl paraben | 0.08 |
| Propyl paraben | 0.02 |
| Citric acid | 0.3 |
| Sodium citrate | 0.15 |
| EDTA | 0.05 |
| Water | q.s. to 100% |

[1]Hydroxypropyl methylcellulose; 7-12% hydroxypropyl, 19-24% methoxyl, 80,000-120,000 cP apparent viscosity of 2% in water at 20° C.

In addition, a terconazole gel containing 0.8% by weight terconazole was prepared from the components listed in Table 3, below.

TABLE 3

| Ingredient | Percentage |
| --- | --- |
| Terconazole | 0.8 |
| MethoCel K 100M | 2 |
| Propylene glycol | 5 |
| Methyl paraben | 0.08 |
| Propyl paraben | 0.02 |
| Citric acid | 0.3 |
| Sodium citrate | 0.15 |
| EDTA | 0.05 |
| Water | q.s. to 100% |

The release of terconazole from this 0.8% gel was evaluated against a commercially available 0.8% terconazole cream. Approximately 0.5 g of each composition was placed in separate, previously wetted dialysis tubes, and the ends of the tubes were closed with plastic clips. Each dialysis tube was placed in a separate Petri dish containing about 20 mL of 1 millimolar citric acid in a 0.9 percent by weight sodium chloride solution adjusted to about pH 4.25. The Petri dish was then covered with a lid to eliminate evaporation. The Petri dishes were agitated with a magnetic stirrer and about 5 mL samples were withdrawn for assay at appropriate time intervals. The sample volume was replaced with an equal volume of blank medium (i.e., 0.9 percent saline with 1 mmol citric acid). The samples were assayed by UV spectroscopy at 230 nm (the wavelength maximum for terconazole) to determine the concentration of terconazole released from the compositions in the dialysis tubes. The concentration of terconazole in each sample was calculated using a calibration curve. Plots of the percentage of terconazole released over time for the gel composition of the invention and the commercial cream are shown in FIG. 1.

The 0.8% terconazole gel composition of the invention surprisingly released over 90% of the terconazole within five hours, and substantially all of the terconazole within 10 hours (see FIG. 1, upper curve). In contrast, the commercially available 0.8% terconazole cream released only about 25% of the terconazole within five hours and only about 57% of the terconazole within 23 hours (see FIG. 1, lower curve).

EXAMPLE 3

Aqueous Terconazole Solutions

Aqueous solutions containing terconazole (molecular weight 532.48) and citric acid (molecular weight 192.12) were prepared as shown in Table 4, below.

TABLE 4

| Terconazole Concentration (w/w) | Terconazole:Citric Acid Mole Ratio | Terconazole Actual Weight (milligrams) | Citric Acid Actual Weight (milligrams) | Final Solution Weight (Grams) |
| --- | --- | --- | --- | --- |
| 0.4% | 1:0.5 | 401 | 73 | 100 |
| 0.4% | 1:1 | 201 | 72 | 50 |
| 0.4% | 1:1.5 | 200 | 110 | 50 |
| 0.6% | 1:1 | 303 | 103 | 50 |
| 0.6% | 1:1.5 | 302 | 162 | 50 |
| 0.8% | 1:0.5 | 807 | 145 | 100 |
| 0.8% | 1:1 | 408 | 145 | 50 |
| 0.8% | 1:1.5 | 402 | 212 | 50 |
| 1% | 1:1 | 503 | 183 | 50 |
| 1% | 1:1.5 | 502 | 272 | 50 |
| 2% | 1:1 | 1040 | 360 | 50 |
| 2% | 1:1.5 | 1010 | 544 | 50 |
| 3% | 1:0.5 | 1506 | 271 | 50 |
| 3% | 1:1 | 1505 | 541 | 50 |
| 3% | 1:1.5 | 1506 | 810 | 50 |

The prepared solutions were poured into clear glass vials, stored at room temperature, and observed for the presence or absence of crystals. The solutions were checked for crystals immediately after preparation, after 48 hours storage, and after 72 hours storage. The observations are noted in Table 5, below.

TABLE 5

| Terconazole Concentration | Terconazole:Citric Acid Mole Ratio | Crystals @ Time 0 | Crystals @ 48 Hours | Crystals @ 72 Hours |
| --- | --- | --- | --- | --- |
| 0.4% | 1:05 | Absent | Absent | Absent |
| 0.4% | 1:1 | Absent | Absent | Absent |
| 0.4% | 1:1.5 | Absent | Absent | Absent |
| 0.6% | 1:1 | Absent | Absent | Absent |
| 0.6% | 1:1.5 | Absent | Absent | Absent |
| 0.8% | 1:0.5 | Absent | Absent | Absent |
| 0.8% | 1:1 | Absent | Absent | Absent |
| 0.8% | 1:1.5 | Absent | Absent | Absent |
| 1% | 1:1 | Absent | Absent | Absent |
| 1% | 1:1.5 | Absent | Absent | Absent |
| 2% | 1:1 | Absent | Absent | Absent |
| 2% | 1:1.5 | Absent | Absent | Absent |
| 3% | 1:0.5 | Absent | Absent | Absent |
| 3% | 1:1 | Absent | Absent | Absent |
| 3% | 1:1.5 | Absent | Absent | Absent |

As can be seen from Table 5, the prepared solutions were free from crystalline material.

EXAMPLE 4

Aqueous Terconazole Gel

An aqueous terconazole gel composition containing 0.8 percent by weight terconazole and about 149 mole percent of citric acid, based on the number of moles of terconazole present, was prepared and checked for the presence of crystals. The composition ingredients are listed in Table 6, below.

TABLE 6

| Ingredient | Amount, wt.-% |
| --- | --- |
| Terconazole | 0.8 |
| Hydroxypropyl methyl cellulose | 2.5 |
| Propylene glycol | 3.0 |
| Methyl paraben | 0.08 |
| Propyl paraben | 0.02 |

TABLE 6-continued

| Ingredient | Amount, wt.-% |
| --- | --- |
| EDTA | 0.05 |
| L-methionine | 0.18 |
| Citric acid | 0.43 |
| Sodium citrate | q.s. to pH 4 |
| Purified water | q.s. to 100 |

The prepared aqueous terconazole gel containing the ingredients shown in Table 6, above, was observed under an Olympus® light microscope at 40× magnification after 11 months storage at room temperature. No crystals were found to be present.

The compositions of the invention provide a significant improvement for the treatment of vaginal yeast infections, because they provide rapid and nearly complete release of the terconazole, compared to commercial products, which contained undissolved terconazole. The relatively high levels of soluble terconazole provided by the compositions of the invention provide for rapid killing of pathogens.

Numerous variations and modifications of the embodiments described above may be effected without departing from the spirit and scope of the novel features of the invention. No limitations with respect to the specific embodiments illustrated herein are intended or should be inferred.

We claim:

1. An aqueous terconazole composition comprising at least about 0.4 percent by weight of terconazole dissolved in water containing at least 35 mole percent of citric acid based on the number of moles of terconazole present in the composition; the composition being free from terconazole crystals at an ambient temperature of about 20° C. or greater.

2. The composition of claim 1 containing about 50 to about 150 mole percent of citric acid.

3. The composition of claim 1 containing about 0.8 to about 3 percent by weight of terconazole dissolved in the water.

4. The composition of claim 1 wherein the citric acid is present in the composition in a molar amount at least equal to the molar amount of terconazole present in the composition.

5. The composition of claim 1 further comprising a thickening agent.

6. The composition of claim 5 wherein the thickening agent comprises a hydroxypropyl methylcellulose.

7. A method for preparing a solution comprising at least about 0.4 percent by weight of terconazole dissolved in water, free from terconazole crystals at an ambient temperature of about 20° C., the method comprising dissolving terconazole in an aqueous solution containing a terconazole crystallization-inhibiting amount of citric acid.

8. The method of claim 7 wherein the aqueous solution contains at least 35 mole percent of citric acid, based on the number of moles of terconazole present.

9. The method of claim 7 wherein the citric acid is present in the aqueous solution at a concentration in the range of about 50 to about 150 mole percent based upon the molar amount of terconazole dissolved.

10. The method of claim 7 wherein the citric acid is present in the solution in a molar amount at least equal to the molar amount of terconazole dissolved.

11. The method of claim 7 wherein the solution contains about 0.4 to about 3 percent by weight of terconazole.

* * * * *